(12) United States Patent
Matsui

(10) Patent No.: US 8,279,276 B2
(45) Date of Patent: Oct. 2, 2012

(54) RECEIVING APPARATUS

(75) Inventor: Akira Matsui, Hino (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 1016 days.

(21) Appl. No.: 12/174,372

(22) Filed: Jul. 16, 2008

(65) Prior Publication Data

US 2008/0278575 A1    Nov. 13, 2008

Related U.S. Application Data

(63) Continuation of application No. PCT/JP2007/056232, filed on Mar. 26, 2007.

(30) Foreign Application Priority Data

Mar. 24, 2006    (JP) .................................. 2006-081950

(51) Int. Cl.
    *G03B 13/00* (2006.01)
(52) U.S. Cl. .......................................... 348/72; 348/65
(58) Field of Classification Search ...................... 348/72
    See application file for complete search history.

(56) References Cited

U.S. PATENT DOCUMENTS

| | | | | | |
|---|---|---|---|---|---|
| 5,178,130 | A | * | 1/1993 | Kaiya ............................ | 600/109 |
| 5,209,220 | A | * | 5/1993 | Hiyama et al. ................. | 600/109 |
| 6,154,248 | A | * | 11/2000 | Ozawa et al. .................... | 348/65 |
| 2002/0118278 | A1 | | 8/2002 | Kobayashi et al. | |
| 2003/0085994 | A1 | * | 5/2003 | Fujita et al. ...................... | 348/77 |
| 2006/0004253 | A1 | | 1/2006 | Shigemori et al. | |
| 2007/0058036 | A1 | | 3/2007 | Shigemori et al. | |
| 2007/0270781 | A1 | * | 11/2007 | Burgermeister et al. ..... | 604/528 |

FOREIGN PATENT DOCUMENTS

| | | |
|---|---|---|
| CN | 1701752 A | 11/2005 |
| JP | 2002-253493 | 9/2002 |
| JP | 2003-019111 | 1/2003 |
| JP | 2005-118159 | 5/2005 |
| JP | 2005-304595 | 11/2005 |
| JP | 2005-334081 | 12/2005 |
| JP | 2006-075537 | 3/2006 |
| WO | WO 2005/048825 A1 | 6/2005 |

OTHER PUBLICATIONS

English translation for JP 2004-122653, filed on Apr. 2004 in Japan. Assignee: Olympus.*
Chinese Office Action dated Dec. 4, 2009.
English language abstract only of Japanese Patent Application Publication No. JP 2005-304595.

* cited by examiner

*Primary Examiner* — Hieu Hoang
*Assistant Examiner* — Tauqir Hussain
(74) *Attorney, Agent, or Firm* — Scully, Scott, Murphy & Presser, P.C.

(57) ABSTRACT

A receiving apparatus includes a receiver, a signal processor, an identifying unit, and a processing determining unit. The receiver receives serial data transmitted from a body-insertable apparatus, the serial data including a payload portion that indicates actual content of the serial data and an additional portion that is added to the payload portion as a signal indicating a position to start processing and contains attribute information that varies according to each type of body-insertable apparatus. The signal processor performs predetermined signal processing on the payload portion of the serial data. The identifying unit identifies a type of the body-insertable apparatus based on the attribute information contained in the additional portion of the serial data. The processing determining unit selects a mode of signal processing performed on the payload portion by the signal processor based on an identification result obtained by the identifying unit.

7 Claims, 7 Drawing Sheets

RECEIVING APPARATUS

CROSS-REFERENCE TO RELATED APPLICATIONS

This application is a continuation of PCT international application Ser. No. PCT/JP2007/056232 filed Mar. 26, 2007 which designates the United States, incorporated herein by reference, and which claims the benefit of priority from Japanese Patent Application No. 2006-081950 filed Mar. 24, 2006, incorporated herein by reference.

BACKGROUND OF THE INVENTION

1. Field of the Invention

The present invention relates to a receiving apparatus that performs predetermined processing on information transmitted from a body-insertable apparatus such as a capsule endoscope that is introduced into the subject's body to acquire in-vivo information.

2. Description of the Related Art

In recent years, in the field of the endoscope, capsule endoscopes have been proposed that are provided with an imaging function and a radio communication function. During an observation period after this type of capsule endoscope is swallowed by a subject (human body) from the mouth for observation (examination) until it is naturally excreted from the body, the capsule endoscope travels inside the organs (in the body cavity), such as the esophagus, stomach and small intestine, along with their peristaltic motion. While traveling, the capsule endoscope successively captures images with the imaging function.

During the observation period in which the capsule endoscope travels inside the organs, image data captured by the capsule endoscope in the body cavity are successively transmitted via radio to the outside of the subject's body with the radio communication function, and stored in a memory of an external receiving apparatus. By carrying a receiving apparatus having the radio communication function and memory function, the subject is allowed to act freely without constraint even during the observation period after swallowing the capsule endoscope until excreting it. After the observation period, body cavity images are displayed on a display unit based on the image data stored in the memory of the receiving apparatus to allow a diagnosis to be made (see, for example, Japanese Patent Application Laid-open No. 2003-19111). Among such capsule endoscopes are those applied to a specific part as a target to capture an image from, including an esophagus capsule endoscope and a small-intestine capsule endoscope, which capture an image once reaching their target organ.

SUMMARY OF THE INVENTION

A receiving apparatus according to an aspect of the present invention includes a receiver that receives serial data transmitted from a body-insertable apparatus, the serial data including a payload portion that indicates actual content of the serial data and an additional portion that is added to the payload portion as a signal indicating a position to start processing and contains attribute information that varies according to each type of body-insertable apparatus. The receiving apparatus also includes a signal processor that performs predetermined signal processing on the payload portion of the serial data; an identifying unit that identifies a type of the body-insertable apparatus based on the attribute information contained in the additional portion of the serial data; and a processing determining unit that selects a mode of signal processing performed on the payload portion by the signal processor based on an identification result obtained by the identifying unit.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a receiving apparatus according to the present invention are explained in detail below with reference to the accompanying drawings. It is to be understood that the present invention is not limited to the embodiments but is susceptible to various changes and modifications without departing from the spirit and scope thereof.

Figure 1:
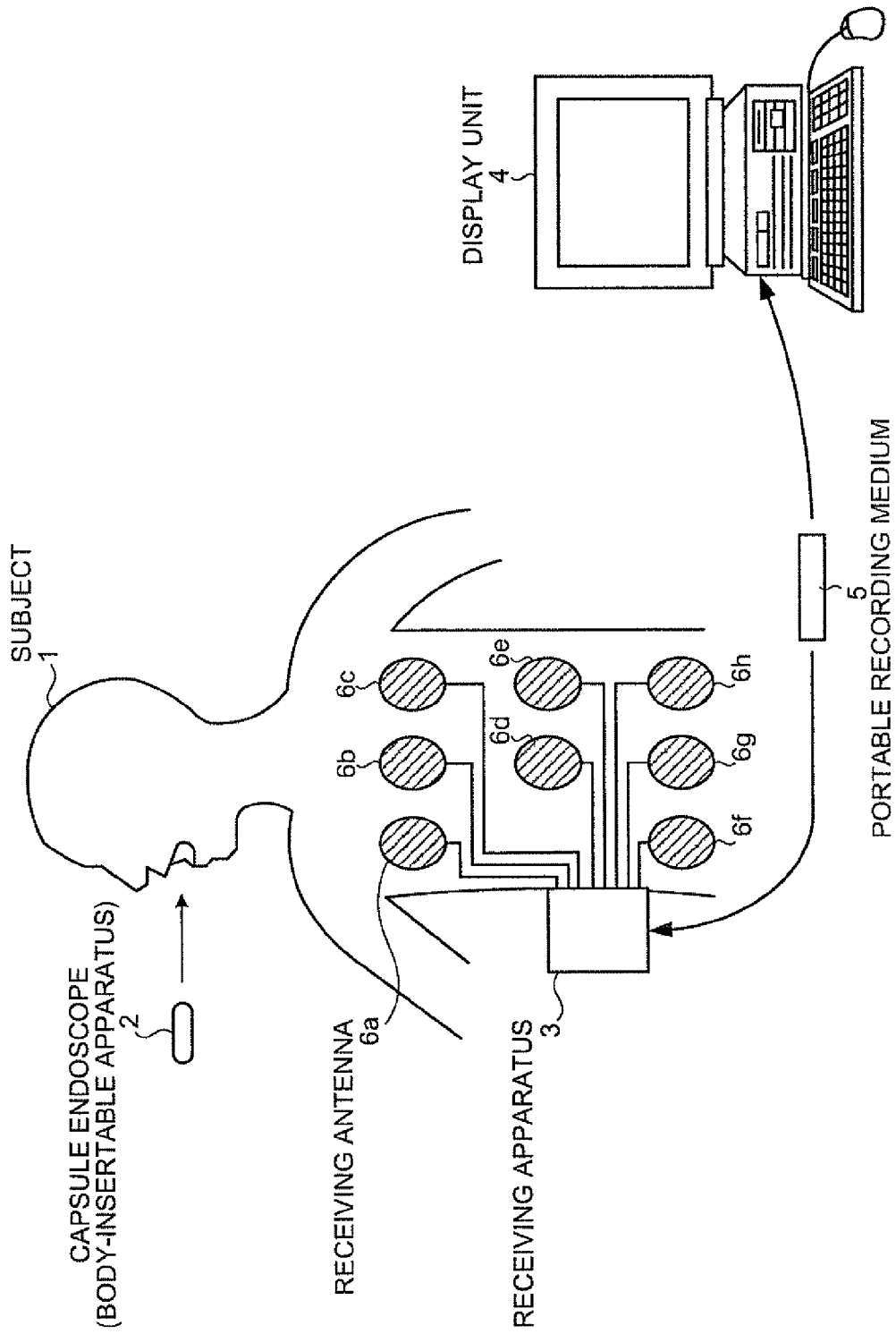
FIG. 1 is a schematic diagram showing the entire configuration of a body-insertable apparatus system that includes a receiving apparatus according to a first embodiment.

FIG. 1 is a schematic diagram showing the entire configuration of a body-insertable apparatus system that includes a receiving apparatus according to a first embodiment of the present invention. As shown in FIG. 1, the body-insertable apparatus system of the first embodiment includes a capsule endoscope 2, a receiving apparatus 3, a display unit 4, and a portable recording medium 5. After being introduced into the body of a subject 1, the capsule endoscope 2 travels along its route. The receiving apparatus 3 receives a radio signal including in-vivo information transmitted from the capsule endoscope 2. The display unit 4 displays an image based on the in-vivo information included in the radio signal received by the receiving apparatus 3. The receiving apparatus 3 and the display unit 4 exchange data with each other through the portable recording medium 5.

The display unit 4 displays an in-vivo image captured by the capsule endoscope 2 and received by the receiving apparatus 3, and the like. The display unit 4 has such a configuration as a workstation that displays an image based on data obtained from the portable recording medium 5. More specifically, the display unit 4 can be configured to directly display an image, etc. on a CRT display, a liquid crystal display, or the like. Alternatively, the display unit 4 may be configured to output an image, etc. through another medium such as a printer.

The portable recording medium 5 can be, for example, a CompactFlash® memory, and is connectable to and disconnectable from the receiving apparatus 3 and the display unit 4. The portable recording medium 5 is configured such that, when connected to any one of the two, it is capable of outputting or storing information. More specifically, while the capsule endoscope 2 travels in the body cavity of the subject 1, the portable recording medium 5 is connected to the receiving apparatus 3 to store in-vivo images. After the capsule endoscope 2 is excreted from the subject 1, the portable recording medium 5 is ejected from the receiving apparatus 3 and connected to the display unit 4, so that the display unit 4 can read data stored in the portable recording medium 5. Such a data exchange between the receiving apparatus 3 and the display unit 4 via the portable recording medium 5 allows the subject 1 to act freely even while the capsule endoscope 2 is traveling inside the body. This advantageously differs from the case where the receiving apparatus 3 and the display unit 4 are connected via wire.

For example, a loop antenna is used to form receiving antennas 6a to 6h. The loop antenna is fixedly attached to the outer body surface of the subject 1 in predetermined places. Preferably, the receiving antennas 6a to 6h are provided with a fixing member for fixing them, i.e., the loop antenna, to the outer body surface of the subject 1.

The capsule endoscope 2 is an example of a body-insertable apparatus. When introduced into the subject 1, the capsule endoscope 2 performs a predetermined function with respect to the subject 1, and communicates via radio with the receiving apparatus 3 located outside the subject 1. More specifically, the capsule endoscope 2 has an imaging function and a function of transmitting acquired data via radio to the receiving apparatus 3.

The capsule endoscope 2 transmits serial data as a radio signal to the receiving apparatus 3. The serial data includes a payload portion that indicates the actual content of the data and an additional portion that is attached to the header of the payload portion as a signal indicating a position to start processing. The additional portion includes a "preamble field" for a preamble signal and a "synchronization signal field" for a synchronization signal. In the first embodiment, the "synchronization signal field" contains attribute information that varies according to the type of the capsule endoscope 2. The "preamble field" is used to ensure a stable reception period when the receiving apparatus 3 starts receiving data, and contains a bit pattern of a predetermined cycle, e.g., "101010 . . . ". The "synchronization signal field" is a field for synchronizing the receipt of data in the payload portion (frame synchronization), and is, as a signal indicating a position to start processing, a signal portion having a pattern that does not appear in a data string within the payload portion.

Some types of capsule endoscopes 2 are exclusively for a specific part to be image-captured, e.g., an esophagus capsule endoscope and a small-intestine capsule endoscope. Among them, for example, a small-intestine capsule endoscope captures images at a frame rate of 2 fps (two frames per second), and performs 8B/10B conversion of captured image data before transmitting or outputting it. Together with the image data, the small-intestine capsule endoscope also transmits parameters such as a capsule ID and a white balance adjustment coefficient.

On the other hand, an esophagus capsule endoscope passes through the specific part at high speed. Therefore, the esophagus capsule endoscope captures images at a frame rate of 18 fps (18 frames per second), and performs data compression and error-correction code addition on captured image data before transmitting it.

Figure 2:
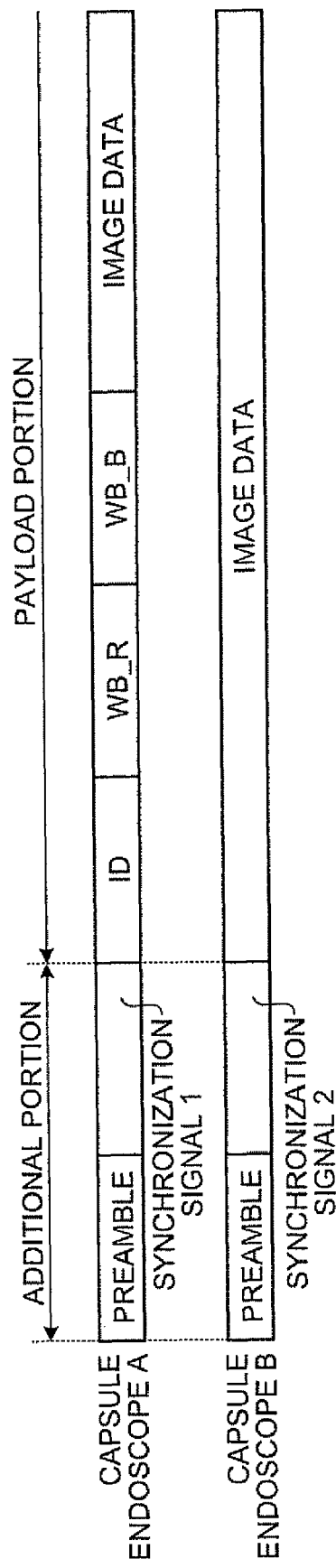
FIG. 2 is an explanatory diagram showing examples of the structure of serial data transmitted from two types of capsule endoscopes A and B.

FIG. 2 is an explanatory diagram showing examples of the structure of data transmitted from two types of capsule endoscopes A and B. For example, the capsule endoscope A is a small-intestine capsule endoscope, and the payload portion of data transmitted therefrom contains a capsule ID, parameters of a white balance adjustment coefficient, and image data. The data in the payload portion has been subjected to 8B/10B conversion, and thus the probabilities of bit "1" and bit "0" are equal.

On the other hand, the capsule endoscope B is an esophagus capsule endoscope. As described above, because of its high-speed travel, the esophagus capsule endoscope is required to capture images at higher speed, as, for example, a frame rate of 18 fps (18 frames per second), compared to the small-intestine capsule endoscope. Since the bandwidth available for transmission of radio signals is limited, i.e., the capsule endoscope transmits data to the receiving apparatus 3 through a limited bandwidth, the capsule endoscope performs data compression on captured data to reduce the volume of the data, thus achieving high-speed data transmission. After undergoing data compression, the image data is subjected to 8B/10B conversion. Further, an error-correction code is added to the image data to correct data errors caused by a radio signal. Thus, the "image data" includes such an error-correction code. The compressed image data in the payload portion is transmitted immediately after a synchronization signal, and other information such as ID information (not shown) is added to the beginning or end of the data as required.

As described above, the payload portion of transmission data varies according to the type of each capsule endoscope in data length, data structure, and format of data stored therein (for example, compressed data, non-compressed data, or data with or without an error-correction code).

In the first embodiment, the "synchronization signal field" of data from the capsule endoscope A is assigned a "synchronization signal 1", while that from the capsule endoscope B is assigned a "synchronization signal 2". The "synchronization signal 1" and the "synchronization signal 2" are both, for example, 40-bit signals, and have different bit patterns according to the difference in type between the capsule endoscopes A and B.

The receiving apparatus 3 is described next. The receiving apparatus 3 receives a radio signal (serial data) transmitted from the capsule endoscope 2, and reassembles data related to an in-vivo image contained in the radio signal as well as storing it.

Figure 3:
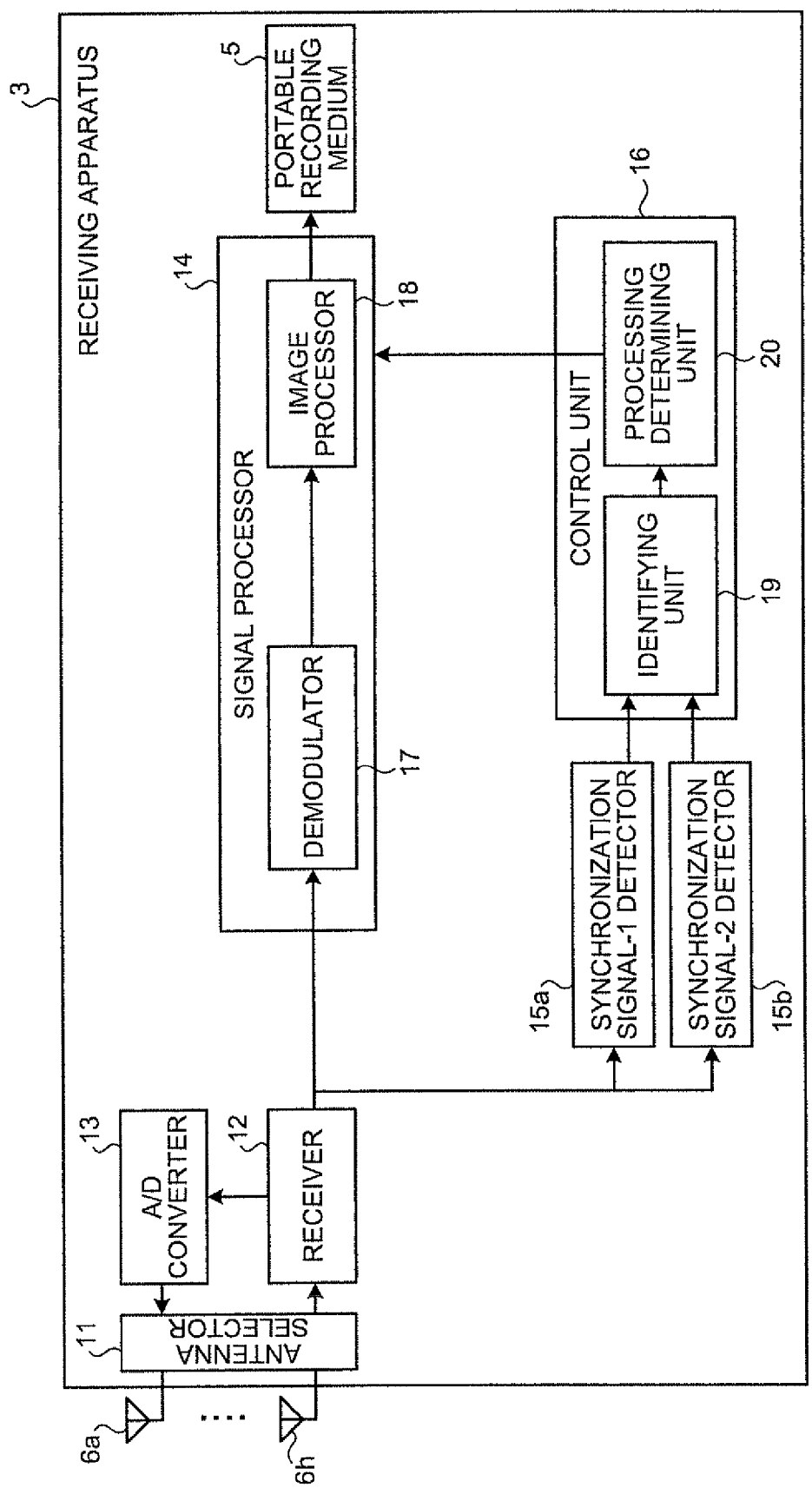
FIG. 3 is a schematic block diagram showing the configuration of the receiving apparatus.

FIG. 3 is a schematic block diagram showing the configuration of the receiving apparatus 3. As shown in FIG. 3, the receiving apparatus 3 includes an antenna selector 11 that selects one of the receiving antennas 6a to 6h suitable for receiving a radio signal; a receiver 12 that demodulates, upon receipt of a radio signal received through one of the receiving antennas 6a to 6h selected by the antenna selector 11, the RF signal to a baseband signal, and outputs it as serial data to the next stage; an A/D converter 13 that converts a received signal strength indicator signal output from the receiver 12 to a predetermined digital signal; a signal processor 14 that performs predetermined signal processing on the serial data output from the receiver 12; and the portable recording medium 5 that stores therein image data subjected to signal processing by the signal processor 14 and the like. The receiving apparatus 3 of the first embodiment further includes a synchronization signal-1 detector 15a, a synchronization signal-2 detector 15b, and a control unit 16. The synchronization signal-1 detector 15a detects a "synchronization signal 1" pattern in the "synchronization signal field" of the serial data output from the receiver 12. The synchronization signal-2 detector 15b detects a "synchronization signal 2" pattern in the "synchronization signal field" of the serial data, and is arranged in parallel with the synchronization signal-1 detector 15a. The control unit 16 identifies the type of the capsule endoscope 2 based on the detection output from the synchronization signal-1 detector 15a and the synchronization signal-2 detector 15b to determine the mode of signal processing performed by the signal processor 14.

The antenna selector 11 selects the most suitable one of the receiving antennas 6a to 6h for receiving a radio signal. The antenna selector 11 outputs a radio signal received through the selected receiving antenna to the receiver 12. More specifically, for example, prior to selecting a receiving antenna, the antenna selector 11 sequentially switches the receiving antennas 6a to 6h to receive radio signals, and outputs the radio signals to the receiver 12. The receiver 12 outputs RSSI (Received Signal Strength Indicator) analog signals to the A/D converter 13. The A/D converter 13 converts the analog signals received from the receiver 12 to digital signals, and outputs the digital signals to the antenna selector 11. Then, the antenna selector 11 selects a receiving antenna corresponding to one of the RSSI digital signals received from the A/D converter 13 that indicates the highest signal strength. Thus, the antenna selector 11 outputs a radio signal received through the selected receiving antenna to the receiver 12.

The signal processor 14 includes, for example, a demodulator 17 and an image processor 18. The demodulator 17 performs demodulation, including serial-to-parallel conversion and 8B/10B conversion (a modulation scheme for equalizing the probabilities of bit "1" and bit "0"), on the payload portion of serial data output from the receiver 12. The image processor 18 performs various types of image processing, such as pixel interpolation, gamma-correction, and JPEG compression, on demodulated parallel data, thus generating data to be stored in the portable recording medium 5. The image processor 18 also generates an image signal to display an image in real time on a display unit, which although is not shown in the drawing, such as LCD.

The control unit 16 includes an identifying unit 19 and a processing determining unit 20. The identifying unit 19 identifies the type of the capsule endoscope 2 based on the detection output from the synchronization signal-1 detector 15a and the synchronization signal-2 detector 15b. More specifically, when the synchronization signal-1 detector 15a detects the "synchronization signal 1" pattern in the "synchronization signal field" of serial data received from a capsule endoscope through the receiver 12, the identifying unit 19 identifies the capsule endoscope as the capsule endoscope A. On the other hand, when the synchronization signal-2 detector 15b detects the "synchronization signal 2" pattern in the "synchronization signal field" of the serial data, the identifying unit 19 identifies the capsule endoscope as the capsule endoscope B.

According to the identification result (the type of the capsule endoscope 2) obtained by the identifying unit 19, the processing determining unit 20 controls the signal processor 14 in such a manner as to select the mode of signal processing performed by the signal processor 14. For example, if the identifying unit 19 identifies the capsule endoscope 2 as the capsule endoscope A, i.e., a small-intestine capsule endoscope, the processing determining unit 20 determines that received serial data has the data structure or format for the capsule endoscope A as shown in FIG. 2. Thus, the processing determining unit 20 reads ID information and white balance adjustment coefficients from a predetermined position of the serial data, and, at the same time, controls the image processor 18 to perform image processing such as image compression and pixel interpolation to reproduce an image and generate an image signal to display the image for real-time observation. In addition, the processing determining unit 20 changes the frequency of a clock signal output from a clock generation circuit (not shown) included in the signal processor 14 so that the image processor 18 operates at an operation frequency of, for example, 16 MHz that achieves processing performance sufficient for image processing at a frame rate of 2 fps. Having selected the mode of signal processing according to the identification result obtained by the identifying unit 19, the processing determining unit 20 exerts control not to change the mode of signal processing thereafter even when a signal is received from a capsule endoscope of a different type, such as the capsule endoscope B.

On the other hand, if the identifying unit 19 identifies the capsule endoscope 2 as the capsule endoscope B, i.e., an esophagus capsule endoscope, the processing determining unit 20 determines that received serial data has the data structure or format for the capsule endoscope B as shown in FIG. 2. Thus, the processing determining unit 20 controls the image processor 18 to perform image processing, such as error correction and decompression of compressed data, to reproduce an image and generate an image signal to display the image for real-time observation. Since the received data has already been compressed, the compressed data is stored directly, without being compressed again, in the portable recording medium 5 before being decompressed.

In addition, the processing determining unit 20 changes the frequency of a clock signal output from a clock generation circuit (not shown) included in the signal processor 14 so that the image processor 18 operates at an operation frequency of, for example, 64 MHz that achieves processing performance sufficient for image processing at a frame rate of 18 fps. Having selected the mode of signal processing according to the identification result obtained by the identifying unit 19, the processing determining unit 20 exerts control not to change the mode of signal processing thereafter even when a signal is received from a capsule endoscope of a different type, such as the capsule endoscope A.

As described above, according to the first embodiment, the type of the capsule endoscope 2 is identified with reference to the pattern of the "synchronization signal field" that varies according to the type of each capsule endoscope. Based on the identification result, the processing determining unit 20 selects the mode of signal processing performed by the signal processor 14 with respect to data in the payload portion. Thus, the one receiving apparatus 3 can handle receipt of serial data from capsule endoscopes having different data structures due to the difference in type between the capsule endoscopes, and is capable of image processing suitable for each type of capsule endoscope.

Moreover, having once selected the mode of signal processing, the processing determining unit 20 exerts control to set (lock) the mode of signal processing not to change it thereafter even when a signal is received from a capsule endoscope of a different type. Therefore, it is possible to prevent, during the receipt of a signal from a certain type of capsule endoscope, the erroneous receipt of a signal from another capsule endoscope of a different type.

Incidentally, in the embodiment described above, having once locked the mode of signal processing, the processing determining unit 20 does not change the mode of signal processing thereafter. However, when, after the processing determining unit 20 locks the mode of signal processing corresponding to a certain type of capsule endoscope, signals are successively received from another capsule endoscope of a different type for a predetermined period of time or more, the processing determining unit 20 can relock the mode of signal processing to the one corresponding to the other capsule endoscope. In this case, even if the processing determining unit 20 erroneously locks the mode of signal processing corresponding to a capsule endoscope of an undesired type, this mode can be reselected as the proper one.

While, in the first embodiment, the pattern of the "synchronization signal field" varies according to the type of each capsule endoscope, an "ID information field" in the payload portion can also contain information related to the type of each capsule endoscope. According to this modification of the first embodiment, for example, with reference to the "synchronization signal field", the capsule endoscope 2 is classified based only on whether the image data is compressed or non-compressed (data coding scheme). If the image data is non-compressed, the capsule endoscope 2 is classified in detail based on ID information contained in the "ID information field".

Figure 4:
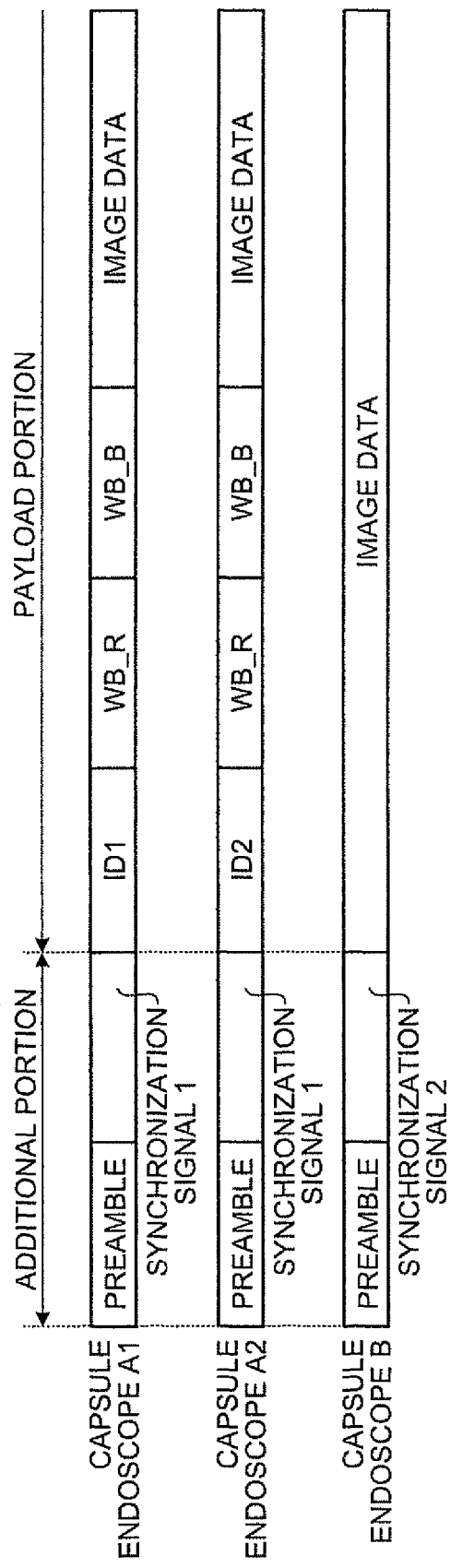
FIG. 4 is an explanatory diagram showing examples of the structure of serial data transmitted from three types of capsule endoscopes A1, A2 and B according to a modification of the embodiment.

FIG. 4 is an explanatory diagram showing examples of the structure of serial data transmitted from three types of capsule endoscopes A1, A2 and B according to the modification. The capsule endoscopes A1 and A2 correspond to the capsule endoscope A described above, and use the same "synchronization signal 1" pattern (indicating non-compressed data); however, "ID information fields" in the payload portions for them contain more detailed information, i.e., "ID1" and "ID2", respectively. Each of "ID1" and "ID2" can includes detailed type information such as correction to be applied that varies according to the characteristics of the optical system of each capsule endoscope, pixel interpolation, defective pixel correction, and compression rate adjustment that vary according to the image size and the characteristics of the CCD of each capsule endoscope.

Figure 5:
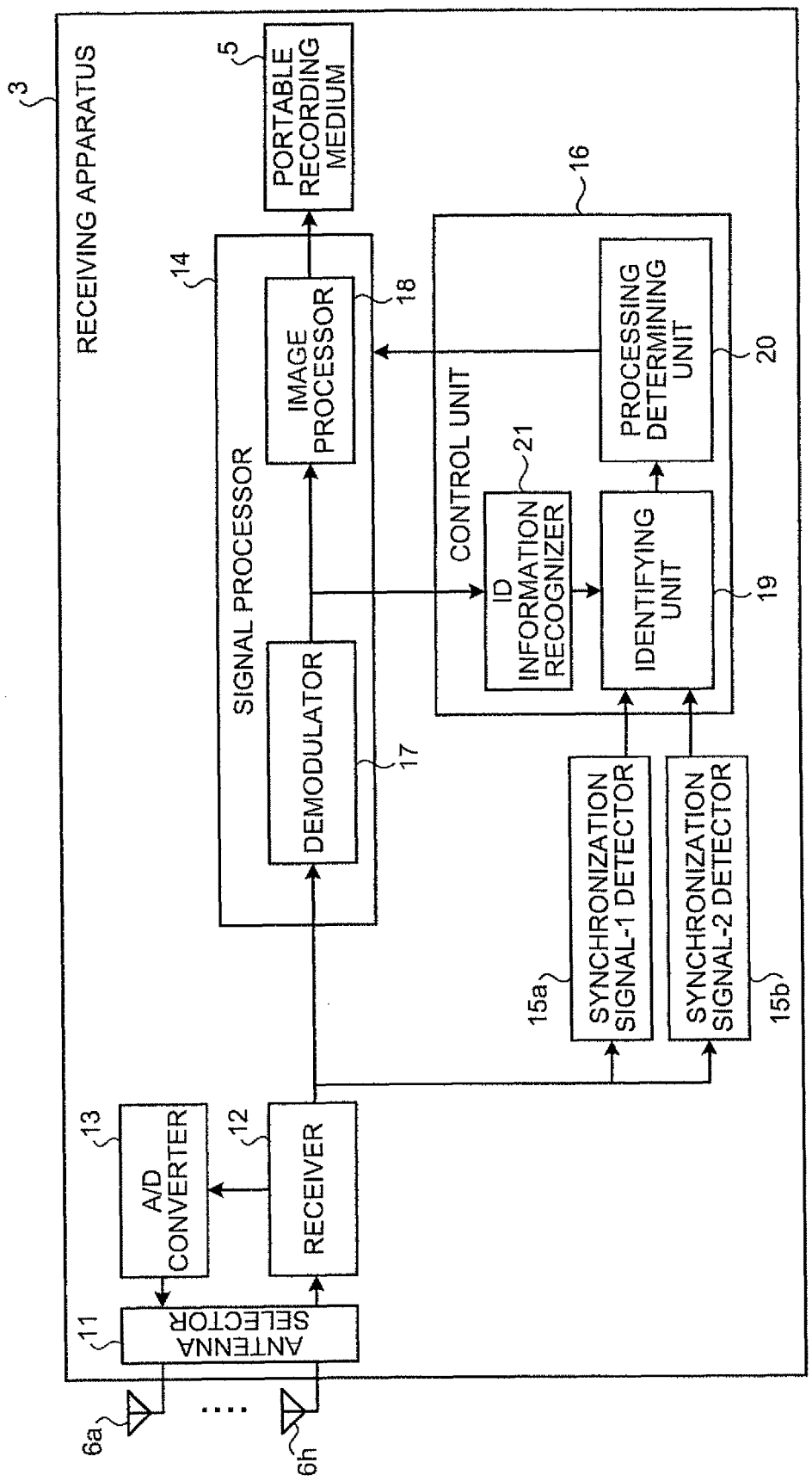
FIG. 5 is a schematic block diagram showing the configuration of a receiving apparatus according to the modification of the embodiment.

FIG. 5 is a schematic block diagram showing the configuration of the receiving apparatus 3 according to the modification. The receiving apparatus 3 shown in FIG. 5 further includes an ID information recognizer 21. The ID information recognizer 21 analyzes, when the synchronization signal-1 detector 15a detects the "synchronization signal 1" pattern, the content of the "ID information field" at the beginning of the payload portion based on the synchronization timing. The identifying unit 19 identifies whether a capsule endoscope is the capsule endoscope A1 or A2 based on the detection result obtained by the synchronization signal-1 detector 15a and the analysis result obtained by the ID information recognizer 21. When the synchronization signal-2 detector 15b detects the "synchronization signal 2" pattern, the identifying unit 19 identifies a capsule endoscope as the capsule endoscope B.

As described above, with the use of the ID information field as well, even for data having basically the same structure such as those transmitted from the capsule endoscopes A1 and A2, the mode of signal processing can be finely modified according to the characteristics of each capsule endoscope. For example, to increase the image size by reducing the frame rate because of the bandwidth limitation, information for selecting an image size is added to "ID1" or "ID2" in the ID information field, so that the image size is to be changed.

While, in the first embodiment, the pattern of the "synchronization signal field" varies according to the type of each capsule endoscope, attribute information in the "preamble field" contained in the additional portion of serial data can be varied instead depending on the type of each capsule endoscope. According to a second embodiment of the present invention, the frequency of a preamble signal (idling pulse) included in the "preamble field" varies according to the type of each capsule endoscope.

Figure 6:
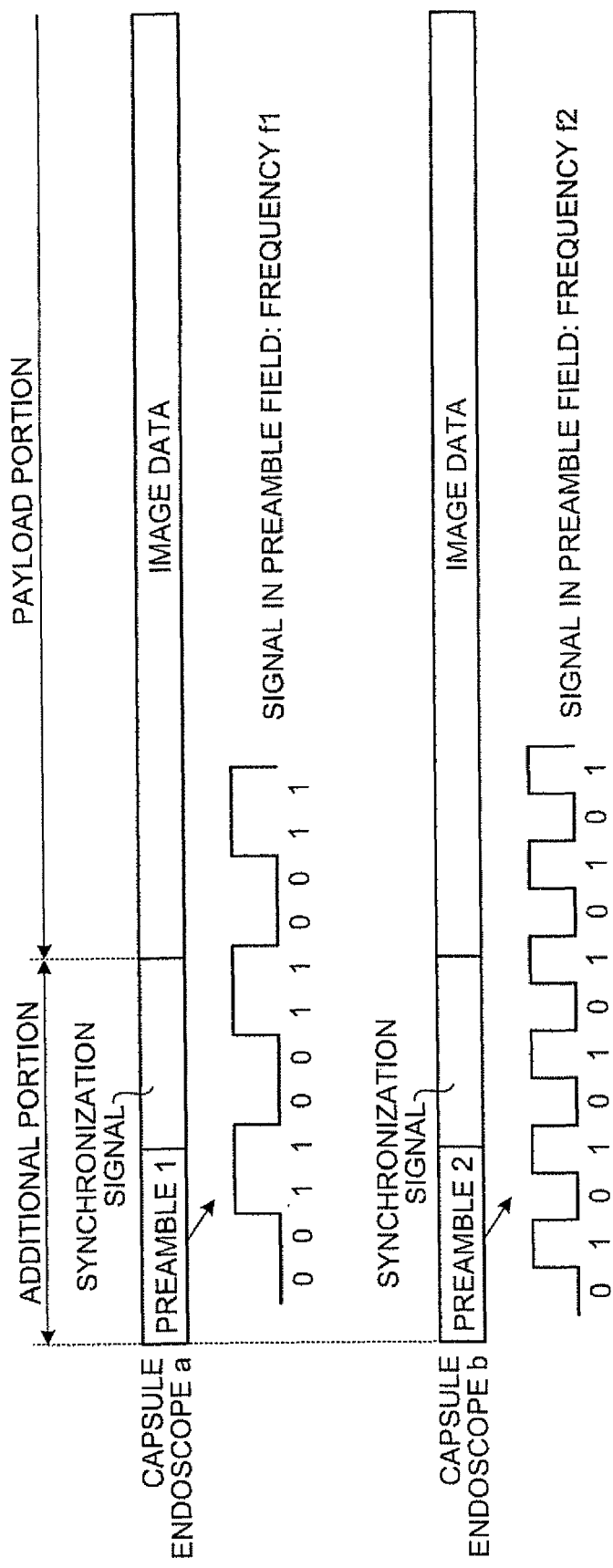
FIG. 6 is an explanatory diagram showing examples of the structure of serial data transmitted from different types of capsule endoscopes a and b, and an example of a preamble signal.

FIG. 6 is an explanatory diagram showing examples of the structure of serial data transmitted from different types of capsule endoscopes a and b, and an example of a preamble signal. In the second embodiment, the "preamble field" of data from the capsule endoscope a is assigned a "preamble signal 1" of frequency f1, while that from the capsule endoscope b is assigned a "preamble signal 2" of frequency f2. For example, it is assumed herein that $2 \times f1 = f2$.

Figure 7:
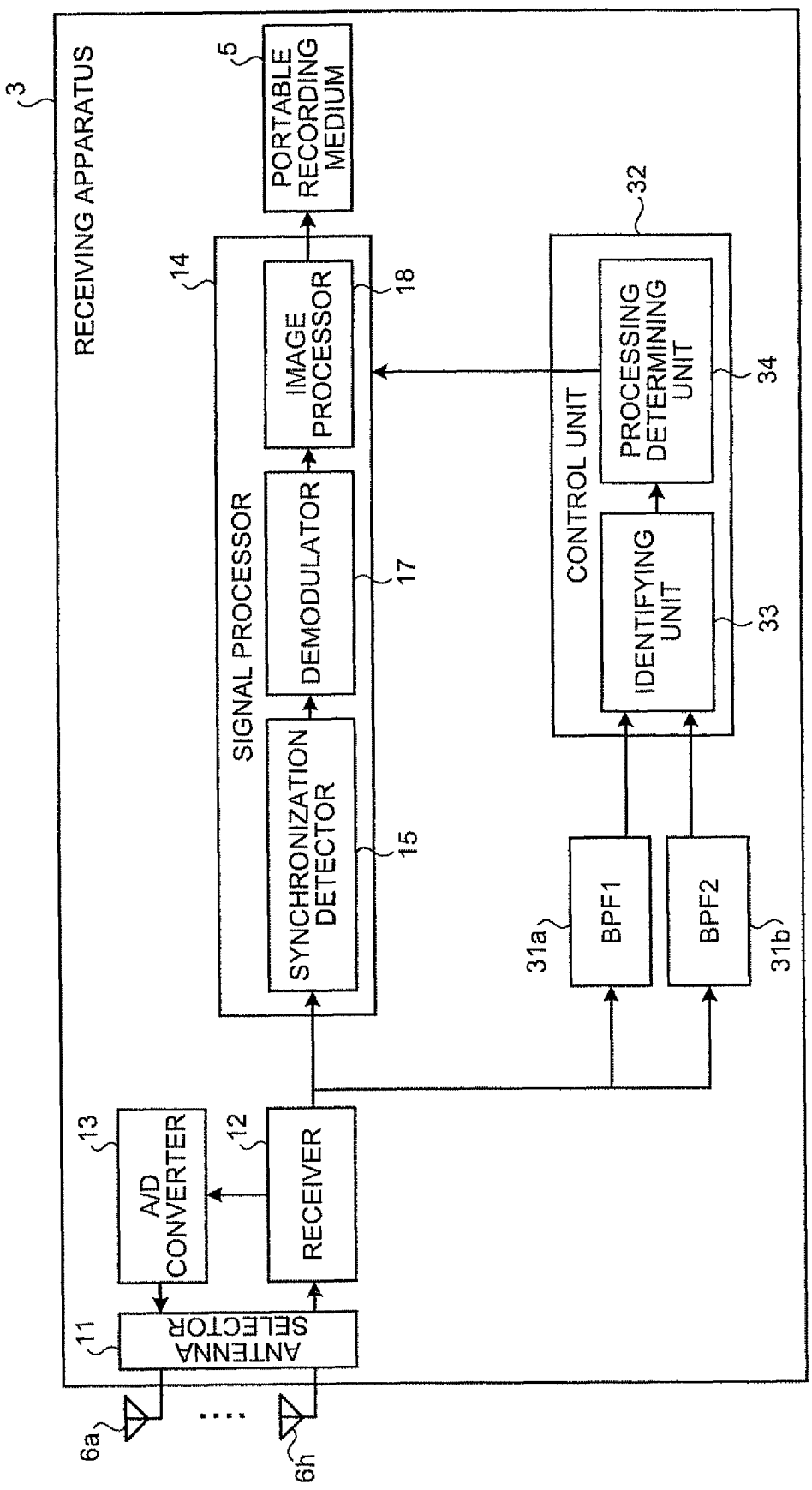
FIG. 7 is a schematic block diagram showing the configuration of a receiving apparatus according to a second embodiment.

FIG. 7 is a schematic block diagram showing the configuration of the receiving apparatus 3 according to the second embodiment. Like reference numerals refer to parts corresponding to those shown in FIG. 3, and the same description is not repeated. The receiving apparatus 3 of the second embodiment includes a bandpass filter (BPF1) 31a, the bandpass frequency of which is set such that the bandpass filter 31a passes the "preamble signal 1" of frequency f1 in the "preamble field" of serial data output from the receiver 12; and a bandpass filter (BPF2) 31b, the bandpass frequency of which is set such that the bandpass filter 31b passes the "preamble signal 2" of frequency f2 in the "preamble field" of serial data output from the receiver 12. The bandpass filters 31a and 31b are arranged in parallel. The receiving apparatus 3 further includes and a control unit 32 that identifies the type of the capsule endoscope 2 based on the output from the bandpass filters 31a and 31b to determine the mode of signal processing performed by the signal processor 14. In the second embodiment, the signal processor 14 includes a synchronization detector 15. The synchronization detector 15 synchronizes to the "synchronization signal field" in the additional portion of serial data, and is used for frame synchronization of the payload portion upon signal processing performed by the signal processor 14.

As with the control unit 16 of the first embodiment, the control unit 32 includes an identifying unit 33 and a processing determining unit 34. The identifying unit 33 identifies the type of the capsule endoscope 2 based on the output from the bandpass filters 31a and 31b. More specifically, when the output of the bandpass filter 31a exceeds a predetermined threshold, the identifying unit 33 identifies a capsule endoscope as the capsule endoscope a. On the other hand, when the output of the bandpass filter 31b exceeds a predetermined threshold, the identifying unit 33 identifies a capsule endoscope as the capsule endoscope b.

According to the identification result (the type of the capsule endoscope 2) obtained by the identifying unit 33, the processing determining unit 34 controls the signal processor 14 in such a manner as to select the mode of signal processing performed by the signal processor 14. The selection of the mode of signal processing is performed in the same manner as previously described in the first embodiment.

As described above, according to the second embodiment, the type of the capsule endoscope 2 is identified by the "preamble field" including a signal at a frequency that varies according to the type of each capsule endoscope. Based on the identification result, the processing determining unit 34 selects the mode of signal processing performed by the signal processor 14 with respect to data in the payload portion. Thus, the one receiving apparatus 3 can handle receipt of serial data from capsule endoscopes having different data structures due to the difference in type between the capsule endoscopes, and is capable of image processing suitable for each type of capsule endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A receiving apparatus comprising:
   a receiver that receives serial data transmitted from a body-insertable apparatus, the serial data including a payload portion that indicates actual content of the serial data and an additional portion that is added to the payload portion as a signal indicating a position to start processing and contains attribute information that varies according to each type of body-insertable apparatus;
   a signal processor that performs predetermined signal processing on the payload portion of the serial data;
   an identifying unit that identifies a type of the body-insertable apparatus based on the attribute information contained in the additional portion of the serial data; and
   a processing determining unit that selects a mode of signal processing performed on the received payload portion by the signal processor based on an identification result obtained by the identifying unit;
   wherein the additional portion includes a preamble field for a preamble signal and a synchronization signal field for a synchronization signal, and the identifying unit identifies the type of the body-insertable apparatus with reference to the synchronization signal field that contains the attribute information in a pattern that varies according to each type of body-insertable apparatus; and
   the receiving apparatus further comprising a plurality of synchronization detectors, each of which detects, in the synchronization signal field, a different pattern that varies according to each type of body-insertable apparatus, wherein the identifying unit identifies the type of the body-insertable apparatus based on which one of the synchronization detectors detects the synchronization signal filed.

2. The receiving apparatus according to claim 1, wherein, after selecting a mode of signal processing, the processing determining unit locks the mode of signal processing not to be changed to another mode of signal processing.

3. The receiving apparatus according to claim 1, wherein the receiver receives the serial data including image data from a first capsule endoscope being the body-insertable apparatus and a second capsule endoscope that is different from the first capsule endoscope in at least one of frame rate for capturing images and data structure of serial data to transmit, and
   the processing determining unit outputs different clock frequencies for the first capsule endoscope and the second capsule endoscope.

4. The receiving apparatus according to claim 1, wherein the payload portion includes an ID information field that contains ID information that varies according to each type of body-insertable apparatus, and
   the identifying unit identifies the type of the body-insertable apparatus based on which one of the synchronization detectors detects the synchronization signal filed and the ID information contained in the ID information field.

5. The receiving apparatus according to claim 1, wherein the additional portion includes a preamble field for a preamble signal and a synchronization signal field for a synchronization signal, and
   the identifying unit identifies the type of the body-insertable apparatus with reference to the preamble field that contains as the attribute information a preamble signal with a frequency that varies according to each type of body-insertable apparatus.

6. The receiving apparatus according to claim 5, further comprising a plurality of bandpass filters, each of which has a different bandpass frequency to detect a preamble signal of a different frequency that varies according to each type of body-insertable apparatus, wherein the identifying unit identifies the type of the body-insertable apparatus based on which one of the bandpass filters detects, in the preamble field, the preamble signal with a frequency that is allowed to pass through the bandpass filter.

7. The receiving apparatus according to claim 1, wherein the processing determining unit changes, as the mode of signal processing, at least one of image size, frame rate, and image processing based on the identification result obtained by the identifying unit.

* * * * *